United States Patent
Lin et al.

(10) Patent No.: US 11,180,611 B2
(45) Date of Patent: Nov. 23, 2021

(54) OLIGOMER OR POLYMER WITH CARBONATE SEGMENT CHEMICAL STRUCTURE

(71) Applicant: J & A TECHNOLOGY CORPORATION, Taipei (TW)

(72) Inventors: Jiang-Jen Lin, Taipei (TW); Tzong-Ming Lee, Chutung (TW); Chyi-Ming Leu, Chutung (TW); Sheng-Yen Shen, Taipei (TW); Hsin-Chung Wu, Chutung (TW); Hsuan-Hao Tien, Taipei (TW)

(73) Assignee: J & A TECHNOLOGY CORPORATION, Taipei (TW)

( * ) Notice: Subject to any disclaimer, the term of this patent is extended or adjusted under 35 U.S.C. 154(b) by 210 days.

(21) Appl. No.: 16/533,875

(22) Filed: Aug. 7, 2019

(65) Prior Publication Data

US 2020/0339752 A1    Oct. 29, 2020

(30) Foreign Application Priority Data

Apr. 25, 2019   (TW) ................. 108114479

(51) Int. Cl.
*C08G 69/44*   (2006.01)
*C07C 69/94*   (2006.01)
*C08G 63/64*   (2006.01)

(52) U.S. Cl.
CPC .............. *C08G 69/44* (2013.01); *C07C 69/94* (2013.01); *C08G 63/64* (2013.01)

(58) Field of Classification Search
CPC ...... C08G 63/64; C08G 63/672; C08G 69/44; C07C 69/94
See application file for complete search history.

(56) References Cited

U.S. PATENT DOCUMENTS

| | | | |
|---|---|---|---|
| 5,559,162 A * | 9/1996 | Meijer | C08G 67/00 522/60 |
| 2012/0184662 A1* | 7/2012 | van der Mee | C08L 51/04 524/451 |
| 2017/0226270 A1* | 8/2017 | Gozin | C08G 18/73 |

* cited by examiner

*Primary Examiner* — Robert S Jones, Jr.
(74) *Attorney, Agent, or Firm* — Schmeiser, Olsen & Watts, LLP

(57) ABSTRACT

An oligomer or polymer with carbonate segment chemical structure, whose structure is expressed by the formula

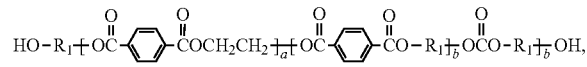

wherein $R_1$ is a functional group derived from a polyol, a polyester polyol or a polyether polyol. The oligomer or polymer with carbonate segment chemical structure is applicable to automobile manufacturing, wires & cables, and medical equipment.

4 Claims, 1 Drawing Sheet

OLIGOMER OR POLYMER WITH CARBONATE SEGMENT CHEMICAL STRUCTURE

CROSS-REFERENCE TO RELATED APPLICATION

This non-provisional application claims priority under 35 U.S.C. § 119(a) on Patent Application No(s).108114479 filed in Taiwan, R.O.C. on Apr. 25, 2019, the entire contents of which are hereby incorporated by reference.

BACKGROUND OF THE INVENTION

1. Field of the Invention

The present disclosure relates to oligomers or polymers, and in particular to an oligomer or polymer with carbonate segment chemical structure.

2. Description of the Related Art

Polycarbonate (PC), an engineering plastic with excellent properties, has advantages as follows: resistant to hydrolysis, high mechanical strength, resistant to impacts, dimensionally stable, resistant to heat, and UV resistant. Therefore, polycarbonate (PC) is widely used in automobile manufacturing, wires & cables, electronic products and medical equipment.

Conventional methods of manufacturing polycarbonate and polycarbonate diol (PCDL) are as follows: 1. ester exchange; 2. phosgenation process; 3. cyclic carbonate ring opening polymerization; 4. carbon dioxide and epoxide polymerization. The phosgene used in the phosgenation process is highly toxic and is a notorious pollutant. A cyclic carbonate with a ring of six or more than six members, which is a required constituent of a raw material for use in the cyclic carbonate ring opening polymerization, is difficult to produce. Furthermore, the ring opening process fails to control the molecular weight of its products. Therefore, at present, polycarbonate diol and polycarbonate are synthesized by ester exchange, wherein polycarbonate diol products are raw materials for use in production of thermoplastic polyurethane.

Conventional polycarbonate (PC) and the other polymeric granules, such as PET granules, PVC granules, and PE granules, are blended and then undergo injection molding to produce PC/PET alloys.

However, there is still room for improvement of conventional polycarbonate (PC) in terms of scope of application, physical and chemical properties, such as elasticity.

BRIEF SUMMARY OF THE INVENTION

In view of the aforesaid drawbacks of conventional polycarbonate (PC), an objective of the present disclosure is to provide an oligomer or polymer with carbonate segment chemical structure.

To achieve at least the above objective, the present disclosure provides an oligomer or polymer with carbonate segment chemical structure, whose structure is expressed by formula I, formula I

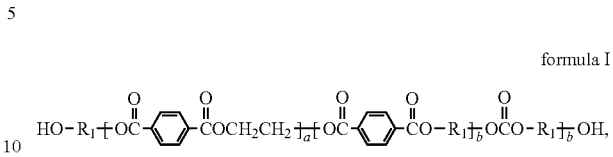

$R_1$ is a functional group derived from a polyol, a polyester polyol or a polyether polyol; a and c are positive integers, and b is 0 or a positive integer.

Regarding the oligomer or polymer with carbonate segment chemical structure, wherein $R_1$ is substituted or unsubstituted, branched or linear, $C_{1-6}$ alkylidene or substituted or unsubstituted, branched or linear, $C_{2-6}$ alkylidene interrupted by —O— or

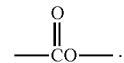

Regarding the oligomer or polymer with carbonate segment chemical structure, wherein $R_1$ is —OH substituted, branched or linear, $C_{1-6}$ alkylidene or —OH substituted, branched or linear, $C_{2-6}$ alkylidene interrupted by —O— or

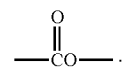

Regarding the oligomer or polymer with carbonate segment chemical structure, wherein a/(a+b+c) ranges from 0.02 to 0.15, b/(a+b+c) is equal to 0; c/(a+b+c) ranges from 0.85 to 0.98. The oligomer or polymer with carbonate segment chemical structure, which meets the aforesaid criteria, is referred to as polyester polycarbonate (PEPC).

Regarding the oligomer or polymer with carbonate segment chemical structure, wherein a/(a+b+c) ranges from 0.85 to 0.98, b/(a+b+c) is equal to 0, and c/(a+b+c) ranges from 0.02 to 0.15. The oligomer or polymer with carbonate segment chemical structure, which meets the aforesaid criteria, is referred to as polycarbonate polyester (PCPE).

Regarding the oligomer or polymer with carbonate segment chemical structure, wherein a/(a+b) ranges from 0.40 to 0.80, b/(a+b) ranges from 0.20 to 0.60, and c/(a+b) ranges from 0.01 to 0.05. In here, the oligomer or polymer with carbonate segment chemical structure, which meets the aforesaid criteria, is referred to as thermoplastic polyester-carbonate elastomer (TPECE).

To achieve at least the above objective, the present disclosure further provides an oligomer or polymer with carbonate segment chemical structure, whose structure is expressed by formula II, formula II

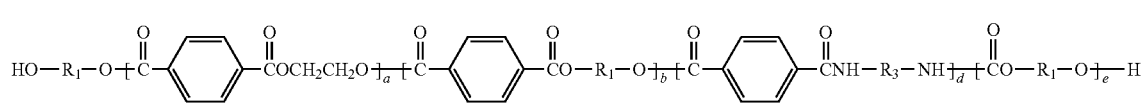

wherein $R_1$ is a functional group derived from a polyol, a polyester polyol or a polyether polyol;

$R_3$ is branched or linear $C_{1-6}$ alkylidene or

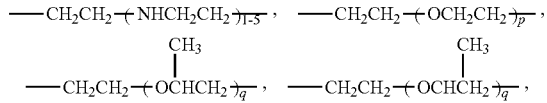

wherein p and q are integers ranging from 3 to 70; and a, b, c and d are positive integers.

Regarding the oligomer or polymer with carbonate segment chemical structure, wherein $R_1$ is substituted or unsubstituted, branched or linear, $C_{1-6}$ alkylidene or substituted or unsubstituted, branched or linear, $C_{2-6}$ alkylidene interrupted by —O— or

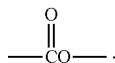

Regarding the oligomer or polymer with carbonate segment chemical structure, wherein $R_1$ is —OH substituted, branched or linear, $C_{1-6}$ alkylidene or —OH substituted, branched or linear, $C_{2-6}$ alkylidene interrupted by —O— or

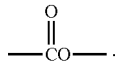

Regarding the oligomer or polymer with carbonate segment chemical structure, wherein a/(a+b) ranges from 0.40 to 0.80, b/(a+b) ranges from 0.20 to 0.60, c/(a+b) ranges from 0.01 to 0.05, and d/(a+b) ranges from 0.01 to 0.20. In here, the oligomer or polymer with carbonate segment chemical structure, which meets the aforesaid criteria, is referred to as thermoplastic polyester-carbonate-amide elastomer (TPEcaE).

To achieve at least the above objective, the present disclosure further provides an oligomer or polymer with carbonate segment chemical structure, whose structure is expressed by formula III or IV,

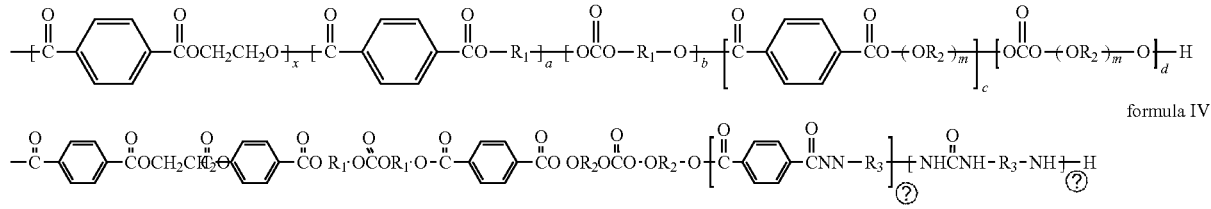

wherein, $R_1$ and $R_2$ are functional groups derived from a polyol, a polyester polyol or a polyether polyol;

$R_3$ is branched or linear $C_{1-6}$ alkylidene or

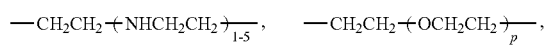

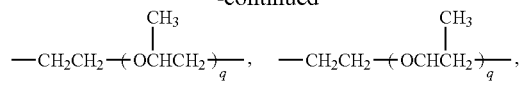

wherein p and q are integers ranging from 3 to 70; and a, b, c, d, e, f, x and m are positive integers.

Regarding the oligomer or polymer with carbonate segment chemical structure, wherein m is an integer ranging from 3 to 50.

Regarding the oligomer or polymer with carbonate segment chemical structure, wherein $R_1$ and $R_2$ are each substituted or unsubstituted, branched or linear, $C_{1-6}$ alkylidene or substituted or unsubstituted, branched or linear, $C_{2-6}$ alkylidene interrupted by —O— or

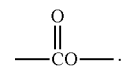

Regarding the oligomer or polymer with carbonate segment chemical structure, wherein $R_1$ and $R_2$ are each —OH substituted, branched or linear, $C_{1-6}$ alkylidene or —OH substituted, branched or linear, $C_{2-6}$ alkylidene interrupted by O— or

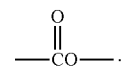

Regarding the oligomer or polymer with carbonate segment chemical structure, wherein, in formula III which expresses the oligomer or polymer with carbonate segment chemical structure, x/(x+a+b+c+d) ranges from 0.500 to 0.995, a+b/(x+a+b+c+d) is greater than or equal to 0 but less than 0.500, c+d/(x+a+b+c+d) is greater than 0 but less than or equal to 0.500; wherein, in formula IV which expresses the oligomer or polymer with carbonate segment chemical structure, x/(x+a+b+c+d+e+f) ranges from 0.500 to 0.995, a+b/(x+a+b+c+d+e+f) is greater than or equal to 0 but less than 0.500, c+d/(x+a+b+c+d+e+f) is greater than 0 but less than or equal to 0.500, and e+f/(x+a+b+c+d+e+f) is greater than 0 but less than or equal to 0.500.

The present disclosure provides an oligomer or polymer with carbonate segment chemical structure, which is produced by performing ester exchange between the monomers of cyclic carbonate monomers and at least one diol monomer in the presence of high-molecular-weight polyester (such as, recycled PET) so as to form polycarbonate diol oligomer, which is then incorporated into polyester polymer by ester-exchange reaction, to therefore produce high-molecular-weight oligomer or polymer with carbonate segment chemical structure.

According to the present disclosure, a method of producing the oligomer or polymer with carbonate segment chemical structure comprises the step as follows:

(1) Introduce into a reactor high-molecular-weight polyester solid (including PET or recycled PET scraps), a polyol (such as, diethylene glycol (DEG)), ethylene glycol (EG), a polyester polyol, a polyether polyol (such as PEG, PPG, PTMEG), and ethylene carbonate (EC) or dimethyl carbonate (DMC);

(2) Introduce into the reactor a catalyst such that in the presence of the catalyst the polyols react with the carbonate monomers by one-pot in situ to produce oligomer polycarbonate diol compound (HO—R—OC(O)—O—R—OH), partially substitute for the chemical structure (—O—$R_1$—O—) in the high-molecular-weight polyester, remove, by vacuum distillation-based regulation, alcohol (HO—$R_0$—OH) produced as a result of ester exchange reaction and substitution such that polyester polymer crude products, which are of different molecular weights and contain carbonate groups, are produced from EG ($R_0$=$CH_2CH_2$) in the PET, and introduce the high-molecular-weight crude products into water, so as to obtain the oligomer or polymer with carbonate segment chemical structure.

In the same manufacturing process, optionally, given the vacuum distillation-based regulation, removal of alcohol (HO—$R_0$—OH) decreases, and then the resultant low molecular weight crude products undergo filtration, so as to obtain a carbonate-containing polyester plasticizer and diol.

producing the oligomer or polymer with carbonate segment chemical structure comprises the steps as follows:

(1) Introduce into a reactor high-molecular-weight polyester and reactive oligomer, wherein the high-molecular-weight polyester is expressed by formula (A),

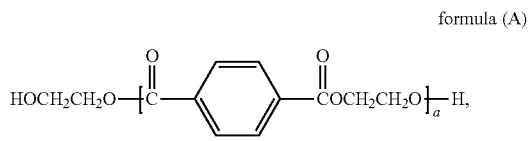

formula (A)

and wherein the reactive oligomer is one selected from the group consisting of poly(polyol) and poly(polyamine);

(2) Introduce into the reactor ethylene carbonate (EC) and a catalyst such that the polyols react with the carbonate monomers by one-pot in situ to form oligomer polycarbonate diol compound (HO—R—OC(O)—O—R—OH), so as to partially substitute for the chemical structure (—O—$R_1$—O—) in the high-molecular-weight polyester and remove by vacuum distillation-based regulation alcohol (HO—$R_0$—OH) produced by ester exchange reaction and substitution, thereby forming a crude product; and (3) Introduce the crude product into water to obtain an oligomer or polymer with carbonate segment chemical structure.

The oligomer or polymer with carbonate segment chemical structure produced by the aforesaid method is expressed by formula I.

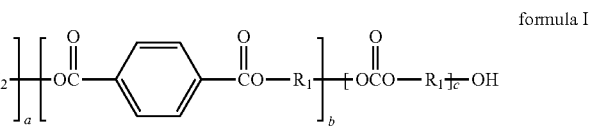

formula I

According to the present disclosure, the oligomer or polymer with carbonate segment chemical structure can form a plasticizer or a thermoplastic elastomer. According to the present disclosure, the plasticizer and diol are applicable to optical film, woodlike construction materials and resins. The thermoplastic elastomer of the present disclosure has excellent physical and chemical properties and thus is applicable to automobile manufacturing, wires & cables, and medical equipment.

DETAILED DESCRIPTION OF THE INVENTION

Figure 1:
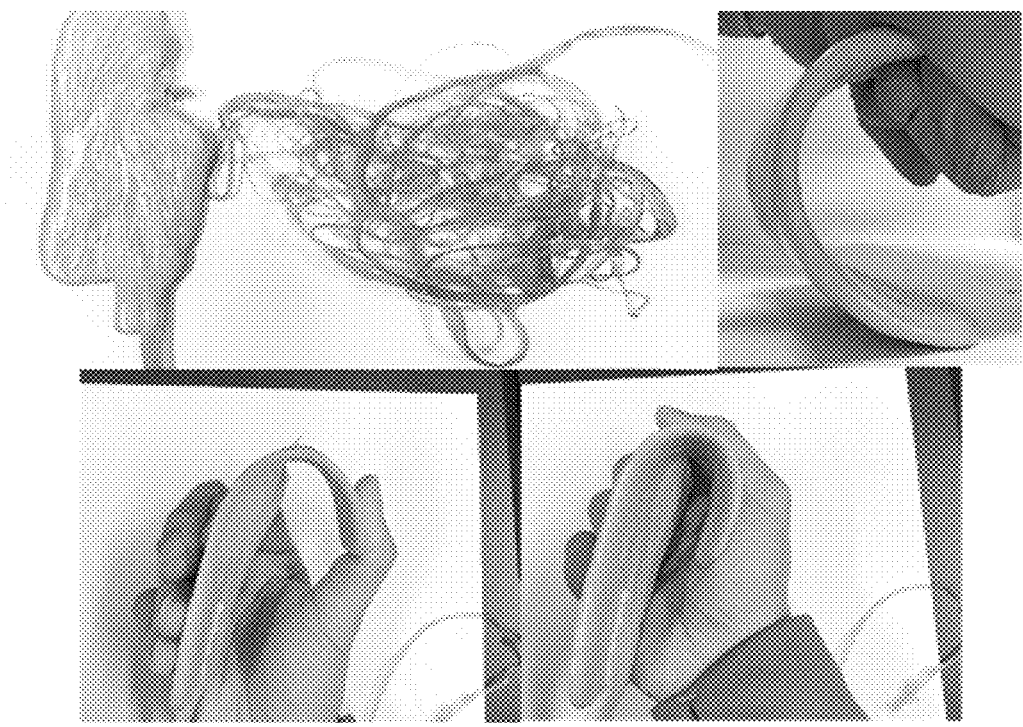
FIG. 1 shows pictures of the bending and appearance of thermoplastic polyester-carbonate elastomer (TPECE) produced in embodiment 1.

To facilitate understanding of the object, characteristics and effects of this present disclosure, embodiments together with the attached drawings for the detailed description of the present disclosure are provided.

The present disclosure provides an oligomer or polymer with carbonate segment chemical structure. A method of In formula I, $R_1$ is a functional group derived from a polyol, a polyester polyol or a polyether polyol.

In step (1), the high-molecular-weight polyester is in the form of solid sheets, particles or powder, which originates from recycled bottles or any other containers made of high-molecular-weight polyester. To be specific, the high-molecular-weight polyester is polyethylene terephthalate (PET), polytrimethylene terephthalate or polybutylene terephthalate.

In the poly(polyol), the number of hydroxyl group is not limited by the present disclosure. For instance, the poly(polyol) is diol, triol or tetraol. Preferably, the molecular weight of the polyether polyol ranges from 250 to 8000 g/mol. To be specific, the poly(polyol) is polytetramethylene ether glycol (PTMEG), poly(propylene glycol), poly(ethylene glycol), polyol (tri-functional poly(oxypropylene) polyol), or a mixture thereof, but the present disclosure is not limited thereto. The poly(oxyalkylene)-diamine is poly(oxypropylene)-diamine or poly(oxyethylene)-diamine, or a mixture thereof, but the present disclosure is not limited thereto. Preferably, the molecular weight of the poly(oxyalkylene)-diamine ranges from 250 to 8000 g/mol. In formula (A), the molecular weight of the poly(oxyalkylene)-diamine preferably ranges from 50 to 500, but the present disclosure is not limited thereto.

In step (1), the catalyst is titanium (Ti) or antimony (Sb), but the present disclosure is not limited thereto. The catalyst may also be magnesium (Mg), aluminum (Al), sodium (Na), potassium (K), any other metallic salt, or organometallic compound.

In step (2), the ethylene carbonate (EC) can be changed to propylene carbonate, dimethyl carbonate, diethyl carbonate, diphenyl carbonate, or a mixture thereof, but the present disclosure is not limited thereto.

The reactive oligomer is one selected from the group consisting of poly(polyol) and poly(polyamine). The poly(polyol) and ethylene carbonate (EC) substitute for the ethylenedioxy (—OCH$_2$CH$_2$O—) in PET by ester exchange; hence, the resultant oligomer or polymer with carbonate segment chemical structure is thermoplastic ester carbonate elastomer (TPECE). In the case of poly(polyamine) and ethylene carbonate (EC), the resultant oligomer or polymer with carbonate segment chemical structure is thermoplastic amide carbonate elastomer (TPACE); and in the presence of a mixture of poly(polyol), poly(polyamine) and ethylene carbonate (EC), the resultant oligomer or polymer with carbonate segment chemical structure is thermoplastic amide ester carbonate elastomer (TPAECE).

In an embodiment of the present disclosure, the oligomer or polymer with carbonate segment chemical structure comprises polyester carbonate elastomer (TPECE) expressed by formula III.

$R_1$ and $R_2$ are functional groups derived from a polyol, a polyester polyol or a polyether polyol; $R_3$ is branched or linear $C_{1-6}$ alkylidene or

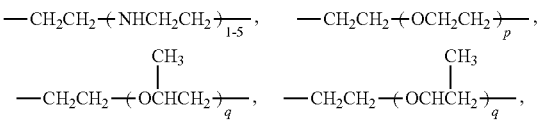

wherein p and q are integers ranging from 3 to 70; and m is an integer ranging from 3 to 50.

Preferably, x+a+b+c+d in formula III ranges from 50 to 500, whereas x+a+b+c+d+e+f in formula IV ranges from 50 to 500, but the present disclosure is not limited thereto.

Regarding the oligomer or polymer with carbonate segment chemical structure, wherein x+a+b+c+d ranges from 10 to 30 such that a plasticizer is formed.

Embodiment 1: thermoplastic elastomer of r-PET/PT-MEG/EC (weight ratio: 68/29/3).

In embodiment 1, the weight ratio of polytetramethylene ether glycol (PTMEG) to polyethylene terephthalate (PET) is 30:70, and, in the presence of 2.7 wt % ethylene carbonate (EC) (molar ratio of PTMEG to EC is 1:1), thermoplastic ester carbonate elastomer (TPECE) is produced.

In embodiment 1, the process flow of producing the thermoplastic elastomer is described below.

A three-necked reactor with a mechanical blender, heater, Dean-Stark Trap, water-cooled condenser and vacuum pump is filled with PTMEG-1000 (105 g, 0.105 mole), EC (9.24 g, 0.105 mole) and titanium (which functions as a catalyst and measures 400 ppm in concentration when compared with the weight of the end product). Then, the three-necked reactor is heated to 150° C. In a blending process, some recycled PET scraps (245 g) are introduced into the three-necked reactor batch by batch. In a blending and heating process, sheets of the PET scraps are dissolved gradually such that more sheets can be introduced. The PET scraps are introduced batch by formula III

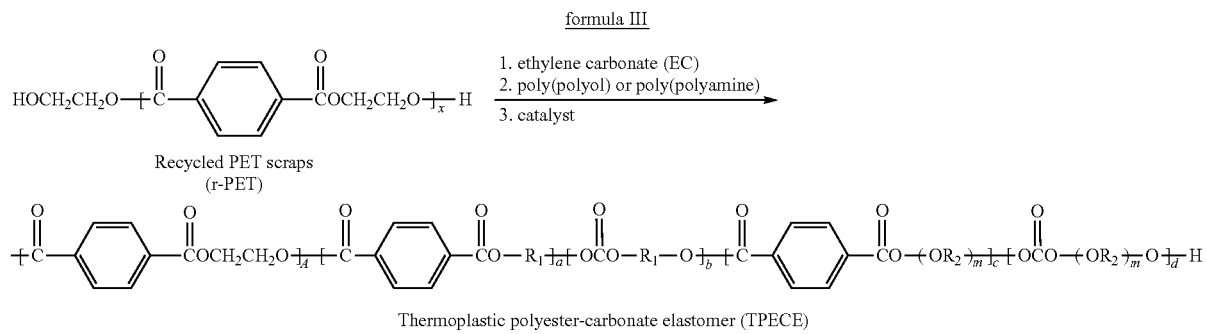

$R_1$ and $R_2$ are functional groups derived from a polyol, a polyester polyol or a polyether polyol; $R_3$ is branched or linear $C_{1-6}$ alkylidene or

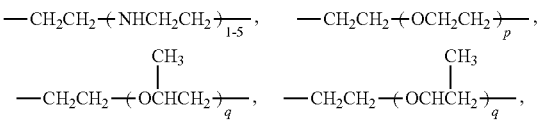

wherein p and q are integers ranging from 3 to 70; and m is an integer ranging from 3 to 50.

Upon simultaneous introduction of poly(polyol) and poly(polyamine), the resultant oligomer or polymer with carbonate segment chemical structure is expressed by formula IV.

formula IV

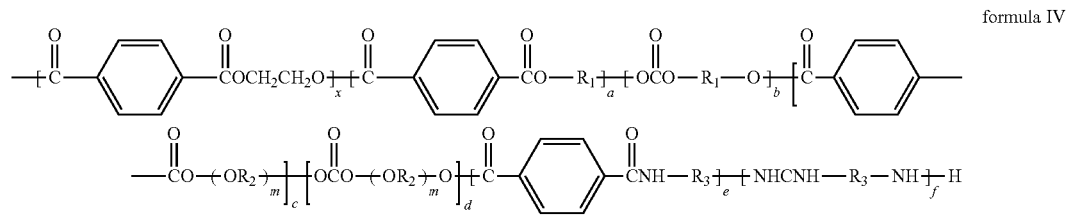

batch according to the dissolution speed. Gradually, the temperature is raised to 250° C. until all the PET sheets are dissolved in the PTMEG. Afterward, the reactor attains a high degree of vacuum (less than 10 torr) with two consecutive pumps. The ethylene glycol (EG) with a low boiling point of 196° C., which polycarbonate diol substitutes for, is removed with the Dean-Stark Trap. At 250° C., the ethylene glycol (EG) is completely removed in three hours, and around 6.51 g of EG is recycled. Then, the product is immediately and quickly introduced into a flask which contains 10 liter of cold water. The product is not only collected in the form of strips but also has high strength and resilience.

FIG. 1 shows the bending and appearance of the thermoplastic polyester-carbonate elastomer produced in embodiment 1.

Embodiment 2: thermoplastic elastomer of r-PET/PTMEG (weight ratio: 70/30).

In embodiment 2, weight ratio of polytetramethylene ether glycol (PTMEG) to polyethylene terephthalate (PET) is 30:70, for example, such that thermoplastic ester elastomer (TPEE) is produced.

In embodiment 2, the process flow of producing the thermoplastic elastomer is described below.

A three-necked reactor with a mechanical blender, heater, Dean-Stark Trap, water-cooled condenser and vacuum pump is filled with PTMEG-1000 (105 g, 0.105 mole) and titanium (which functions as a catalyst and measures 300 ppm in concentration when compared with the weight of the end product). Then, the three-necked reactor is heated to 150° C. In a blending process, some recycled PET scraps (245 g) are introduced into the three-necked reactor batch by batch. In a blending and heating process, sheets of the PET scraps are dissolved gradually such that more sheets can be introduced. The PET scraps are introduced batch by batch according to the dissolution speed. Gradually, the temperature is raised to 250° C. until all the PET sheets are dissolved in the PTMEG. Afterward, the reactor attains a high degree of vacuum (less than 10 torr) with two consecutive pumps. The ethylene glycol (EG) with a low boiling point of 196° C., which PTMEG substitutes for, is removed with the Dean-Stark Trap. At 250° C., the ethylene glycol (EG) is completely removed in three hours, and around 6.51 g of EG is recycled. Then, the product is immediately and quickly introduced into a flask which contains 10 liter of cold water. The product is not only collected in the form of strips but also has resilience.

Figure 2:
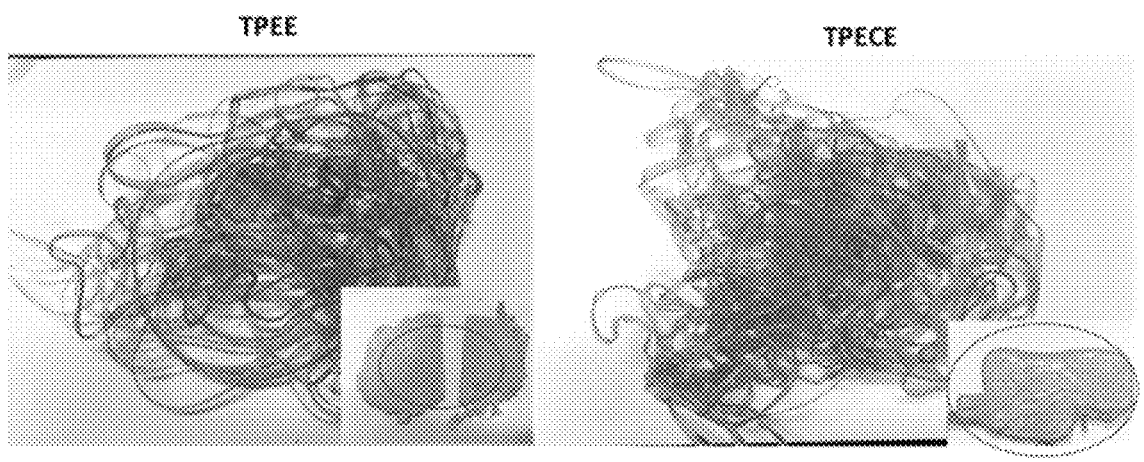
FIG. 2 shows pictures for comparing thermoplastic polyester elastomer (TPEE) produced in embodiment 2 with the TPECE produced in embodiment 1 in terms of bending and appearance.

The thermoplastic ester elastomer (TPEE) in embodiment 2 is produced in the absence of ethylene carbonate (EC). Referring to FIG. 2, TPEE of embodiment 2 has less strength and resilience than TPECE of embodiment 1 and thus is fragile and likely to sever.

Embodiments 3-13 use the same reactive process flow as embodiment 1. Since embodiments 3-12 differ from embodiment 1 in the types and proportions of reactants only, the types and proportions of reactants, rather than the reactive process flow, of embodiments 3-12 are described below.

Embodiment 3: in the presence of PTMEG-650 with a molecular weight of 650, with a weight ratio of PET/PTMEG being 70:30, for example, 2.7 wt % EC is introduced, so as to produce TPECE.

Embodiment 4: in the presence of PTMEG-1000 with a molecular weight of 1000, with a weight ratio of PET/PTMEG being 70:30, for example, 1.3 wt % EC is introduced, so as to produce TPECE.

Embodiment 5: in the presence of PTMEG-1000 with a molecular weight of 1000, with a weight ratio of PET/PTMEG being 70:30, for example, 2.7 wt % EC is introduced, so as to produce TPECE.

Embodiment 6: in the presence of PTMEG-2000 with a molecular weight of 2000, with a weight ratio of PET/PTMEG being 70:30, for example, 1.3 wt % EC is introduced, so as to produce TPECE.

Embodiment 7: in the presence of PTMEG-2000 with a molecular weight of 2000, with a weight ratio of PET/PTMEG being 70:30, for example, 2.7 wt % EC and 0.4 wt % trimethylolpropane (TMP) are introduced, so as to produce TPECE.

Embodiment 8: in the presence of PEG-600 with a molecular weight of 600, with a weight ratio of PET/PEG being 70:30, for example, 1.3 wt % EC is introduced, so as to produce TPECE.

Embodiment 9: in the presence of PEG-1000 with a molecular weight of 1000, with a weight ratio of PET/PEG being 70:30, for example, 2.7 wt % EC is introduced, so as to produce TPECE.

Embodiment 10: in the presence of PEG-2000 with a molecular weight of 2000, with a weight ratio of PET/PEG being 70:30, for example, 1.3 wt % EC is introduced, so as to produce TPECE.

Embodiment 11: in the presence of PET scraps/polyoxypropylene-diamine Jeffamine® D2000 (purchased from Huntsman Corp.), with its weight ratio being 70:30, 2.7 wt % EC is introduced, so as to produce thermoplastic amide carbonate elastomer (TPACE).

Embodiment 12: in the presence of PET scraps and polyoxypropylene-diamine Jeffamine® D2000/PTMEG (purchased from Huntsman Corp.), with its weight ratio being 70:15:15, 2.7 wt % EC is introduced, so as to produce thermoplastic ester carbonate amide elastomer (TPECAE).

Embodiment 13: in the presence of PET scraps and PTMEG1000 with a weight ratio of 70:30, 5 wt % Caprolactam and 1.5 wt % EC are introduced, so as to produce thermoplastic ester carbonate amide elastomer (TPECAE).

Embodiment 14: in the presence of PTMEG-1000 with a molecular weight of 1000, with a weight ratio of PET/PTMEG being 70:30, for example, 2.7 wt % EC and 10 wt % Diethylene glycol are introduced, so as to produce thermoplastic ester carbonate elastomer (TPECE).

Embodiment 15: in the presence of PTMEG-1000 with a molecular weight of 1000, with a weight ratio of PET/PTMEG being 70:30, for example, 2.7 wt % EC, 10 wt % Diethylene glycol and 10 wt % 1,4-butanediol are introduced, so as to produce thermoplastic ester carbonate elastomer (TPECE).

Embodiment 16: in the presence of PTMEG-1000 with a molecular weight of 1000, with a weight ratio of EC/PTMEG/PET being 9/82/9, polyester polycarbonate (PEPC) for oligomer plasticizer is produced.

Embodiment 17: in the presence of PTMEG-1000 with a molecular weight of 1000, with a weight ratio of EC/PTMEG/PET being 4/19/77, polycarbonate polyester (PCPE) for oligomer plasticizer is produced.

Embodiment 18: the aforesaid diol oligomer (PCPE or PEPC) reacts with diisocyanate and 1,4-butanediol to produce thermoplastic polyurethane (TPU).

Compared with the prior art, the present disclosure provides an oligomer or polymer with carbonate segment chemical structure, whose production method entails turning high-molecular-weight polyester into the oligomer or polymer with carbonate segment chemical structure, so as to obtain the oligomer or polymer with carbonate segment chemical structure which is cost-effective enough to degrade high-molecular-weight polyester and perform polymerization anew. According to the present disclosure, the oligomer or polymer with carbonate segment chemical structure is applicable to automobile manufacturing, wires & cables, and medical equipment.

The present disclosure has been described by means of specific embodiments, numerous modifications and variations could be made thereto by those skilled in the art without departing from the scope and spirit of the present disclosure set forth in the claims.

What is claimed is:

1. An oligomer or polymer with carbonate segment chemical structure, whose structure is expressed by formula III or IV,

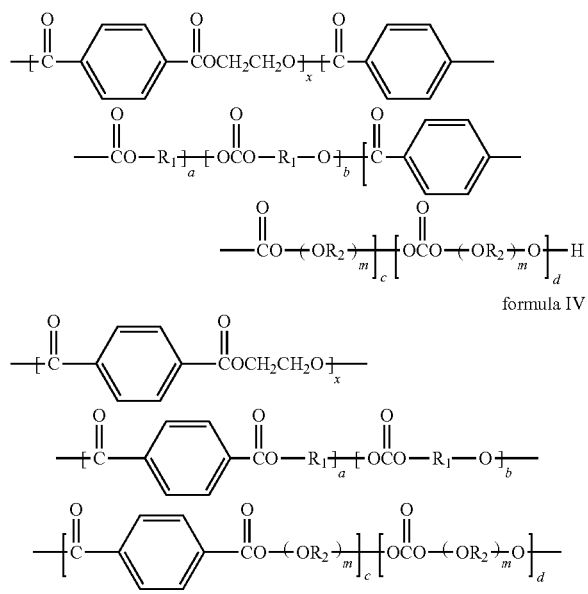

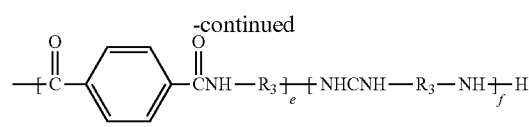

wherein $R_1$ and $R_2$ are functional groups derived from a polyol, a polyester polyol or a polyether polyol, $R_3$ is branched or linear $C_{1-6}$ alkylidene or

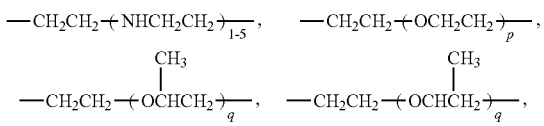

wherein p and q are integers ranging from 3 to 70, and a, b, c, d, e, f, x and m are positive integers.

2. The oligomer or polymer with carbonate segment chemical structure according to claim 1, wherein m is an integer ranging from 3 to 50.

3. The oligomer or polymer with carbonate segment chemical structure according to claim 1, wherein $R_1$ and $R_2$ are each substituted or unsubstituted, branched or linear, $C_{1-6}$ alkylidene or substituted or unsubstituted, branched or linear, $C_{1-6}$ alkylidene interrupted by —O— or

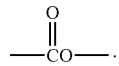

4. The oligomer or polymer with carbonate segment chemical structure according to claim 1, wherein, in formula III, x/(x+a+b+c+d) ranges from 0.500 to 0.995, a+b/(x+a+b+c+d) is greater than or equal to 0 but less than 0.500, c+d/(x+a+b+c+d) is greater than 0 but less than or equal to 0.500, wherein, in formula IV, x/(x+a+b+c+d+e+f) ranges from 0.500 to 0.995, a+b/(x+a+b+c+d+e+f) is greater than or equal to 0 and less than 0.500, c+d/(x+a+b+c+d+e+f) is greater than 0 but less than or equal to 0.500, and e+f/(x+a+b+c+d+e+f) is greater than 0 but less than or equal to 0.500.

* * * * *